United States Patent

Ross, Jr. et al.

(10) Patent No.: US 9,198,428 B2
(45) Date of Patent: Dec. 1, 2015

(54) PROCESSES TO PRODUCE CERTAIN 2-(PYRIDINE-3-YL)THIAZOLES

(71) Applicant: Dow AgroSciences LLC, Indianapolis, IN (US)

(72) Inventors: Ronald Ross, Jr., Zionsville, IN (US); Carl DeAmicis, Indianapolis, IN (US); Yuanming Zhu, Carmel, IN (US); Noormohamed M. Niyaz, Indianapolis, IN (US); Kim E. Arndt, Carmel, IN (US); Scott P. West, Midland, MI (US); Gary Roth, Midland, MI (US)

(73) Assignee: Dow AgroSciences, LLC., Indianapolis, IN (US)

( * ) Notice: Subject to any disclaimer, the term of this patent is extended or adjusted under 35 U.S.C. 154(b) by 74 days.

(21) Appl. No.: 13/905,371

(22) Filed: May 30, 2013

(65) Prior Publication Data

US 2013/0324736 A1 Dec. 5, 2013

Related U.S. Application Data

(60) Provisional application No. 61/655,089, filed on Jun. 4, 2012.

(51) Int. Cl.
*C07D 417/04* (2006.01)
*A01N 43/78* (2006.01)

(52) U.S. Cl.
CPC .............. *A01N 43/78* (2013.01); *C07D 417/04* (2013.01)

(58) Field of Classification Search
USPC ....................................... 546/270.4
See application file for complete search history.

(56) References Cited

U.S. PATENT DOCUMENTS 5,219,824 A 6/1993 Sing et al.
2010/0292253 A1 11/2010 Trullinger et al.

FOREIGN PATENT DOCUMENTS

WO WO2008090382 A1 7/2008
WO PCT/US2013/043208 A1 11/2013

OTHER PUBLICATIONS

Dorwald, Side Reactions in Organic Synthesis, 2005, Wiley: VCH Weinheim Preface, pp. 1-15 & Chapter 8, pp. 279-308.*
Thompson, et al. Ugi Reactions with Ammonia Offer Rapid Access to a Wide Range of 5-Aminothiazole and Oxazole Derivatives. J. Org. Chem. 74(18): 7084-7093, 2009.

* cited by examiner

*Primary Examiner* — Patricia L Morris
(74) *Attorney, Agent, or Firm* — Carl D Corvin

(57) ABSTRACT

The invention disclosed in this document is related to the field of processes to produce certain 2-(pyridine-3-yl)thiazoles as intermediates for the synthesis of pesticidal thiazole amides.

11 Claims, No Drawings

PROCESSES TO PRODUCE CERTAIN 2-(PYRIDINE-3-YL)THIAZOLES

CROSS REFERENCES TO RELATED APPLICATIONS

This Application claims priority from, and benefit of, U.S. provisional application 61/655,089, filed on Jun. 4, 2012. The entire content of this provisional application is hereby incorporated by reference into this Application.

FIELD OF THE DISCLOSURE

The invention disclosed in this document is related to the field of processes to produce certain 2-(pyridine-3-yl)thiazoles as intermediates for the synthesis of pesticidal thiazole amides.

BACKGROUND OF THE DISCLOSURE

Controlling pest populations is essential to modem agriculture, food storage, and hygiene. There are more than ten thousand species of pests that cause losses in agriculture. The world-wide agricultural losses amount to billions of U.S. dollars each year. Pests, such as termites, are also known to cause damage to all kinds of private and public structures resulting in billions of U.S. dollars in losses each year. Pests also eat and adulterate stored food, resulting in billions of U.S. dollars in losses each year, as well as deprivation of food needed for people.

Certain pests have or are developing resistance to pesticides in current use. Hundreds of pest species are resistant to one or more pesticides. Accordingly, there exists a continuous need for new pesticides and for processes of forming such pesticides.

WO 2010/129497 (the entire disclosure of which is incorporated herein) discloses certain pesticides. However, the processes of making such pesticides may be both costly and inefficient. Accordingly, there exists a need for processes of efficiently forming such pesticides.

DEFINITIONS

The examples given in the definitions are generally non-exhaustive and must not be construed as limiting the invention disclosed in this document. It is understood that a substituent should comply with chemical bonding rules and steric compatibility constraints in relation to the particular molecule to which it is attached.

"alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy.

"alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"alkynyloxy" means an alkynyl further consisting of a carbon-oxygen single bond, for example, pentynyloxy, hexynyloxy, heptynyloxy, octynyloxy, nonynyloxy, and decynyloxy.

"aryl" means a cyclic, aromatic substituent consisting of hydrogen and carbon, for example, phenyl, naphthyl, and biphenyl.

"cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, cycloheptenyl, cyclooctenyl, cyclodecenyl, norbornenyl, bicyclo[2.2.2]loctenyl, tetrahydronaphthyl, hexahydronaphthyl, and octahydronaphthyl.

"cycloalkenyloxy" means a cycloalkenyl further consisting of a carbon-oxygen single bond, for example, cyclobutenyloxy, cyclopentenyloxy, cyclohexenyloxy, cycloheptenyloxy, cyclooctenyloxy, cyclodecenyloxy, norbornenyloxy, and bicyclo[2.2.2]octenyloxy.

"cycloalkyl" means a monocyclic or polycyclic, saturated substituent consisting of carbon and hydrogen, for example, cyclopropyl, cyclobutyl, cyclopentyl, cyclohexyl, cycloheptyl, cyclooctyl, cyclodecyl, norbornyl, bicyclo[2.2.2]octyl, and decahydronaphthyl.

"cycloalkoxy" means a cycloalkyl further consisting of a carbon-oxygen single bond, for example, cyclopropyloxy, cyclobutyloxy, cyclopentyloxy, cyclohexyloxy, cycloheptyloxy, cyclooctyloxy, cyclodecyloxy, norbornyloxy, and bicyclo[2.2.2]octyloxy.

"cyclohaloalkyl" means a monocyclic or polycyclic, saturated substituent consisting of carbon halo, and hydrogen, for example, 1-chlorocyclopropyl, 1-chlorocyclobutyl, and 1-dichlorocyclopentyl.

"halo" means fluoro, chloro, bromo, and iodo.

"haloalkyl" means an alkyl further consisting of, from one to the maximum possible number of, identical or different, halos, for example, fluoromethyl, difluoromethyl, trifluoromethyl, 1-fluoroethyl, 2-fluoroethyl, 2,2,2-trifluoroethyl, chloromethyl, trichloromethyl, and 1,1,2,2-tetrafluoroethyl.

"heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen, for example, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, 1,3,4-oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, 1,2,3,4-tetrazolyl, thiazolinyl, thiazolyl, thienyl, 1,2,3-triazinyl, 1,2,4-triazinyl, 1,3,5-triazinyl, 1,2,3-triazolyl, and 1,2,4-triazolyl.

DETAILED DESCRIPTION OF THE DISCLOSURE

An embodiment of this invention is illustrated in Scheme One

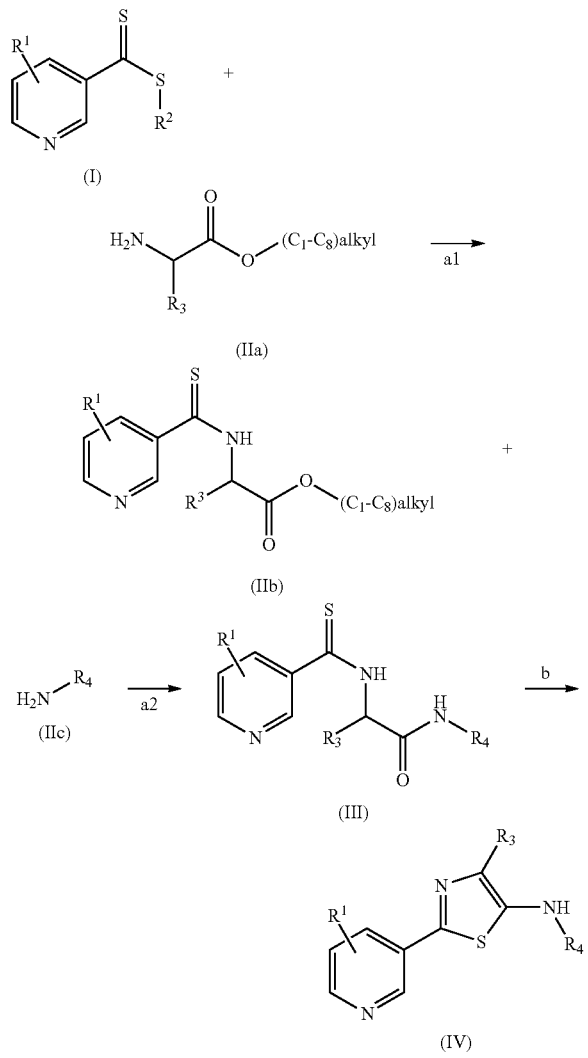

wherein
(A) each $R^1$ is independently selected from H, F, Cl, Br, I, CN, $NO_2$, and substituted or unsubstituted ($C_1$-$C_6$)alkyl, wherein each substituted $R^1$ has one or more substituents independently selected from F, Cl, Br, I, CN, $NO_2$, ($C_1$-$C_6$) alkyl, and ($C_1$-$C_6$)haloalkyl;
(B) $R^2$ is selected from substituted or unsubstituted ($C_1$-$C_6$) alkyl, substituted or unsubstituted ($C_2$-$C_6$)alkenyl, substituted or unsubstituted ($C_1$-$C_6$)alkoxy, substituted or unsubstituted ($C_2$-$C_6$)alkenyloxy, substituted or unsubstituted ($C_3$-$C_{10}$)cycloalkyl, substituted or unsubstituted ($C_3$-$C_{10}$) cycloalkenyl, substituted or unsubstituted ($C_6$-$C_{20}$)aryl, substituted or unsubstituted ($C_1$-$C_6$)alkyl($C_6$-$C_{20}$)aryl, and substituted or unsubstituted ($C_1$-$C_{20}$)heterocyclyl, wherein each substituted $R^2$ has one or more substituents independently selected from F, Cl, Br, I, CN, $NO_2$, ($C_1$-$C_6$) alkyl, ($C_2$-$C_6$)alkenyl, ($C_1$-$C_6$)haloalkyl, ($C_2$-$C_6$)haloalkenyl, ($C_1$-$C_6$)haloalkyloxy, ($C_2$-$C_6$)haloalkenyloxy, ($C_3$-$C_{10}$)cycloalkyl, ($C_3$-$C_{10}$)cycloalkenyl, ($C_3$-$C_{10}$) halocycloalkyl, ($C_3$-$C_{10}$)halocycloalkenyl, ($C_6$-$C_{20}$)aryl, and ($C_1$-$C_{20}$)heterocyclyl;
(C) $R^3$ is selected from H, substituted or unsubstituted ($C_1$-$C_6$)alkyl, substituted or unsubstituted ($C_3$-$C_{10}$)cycloalkyl, substituted or unsubstituted ($C_1$-$C_6$)alkyl($C_3$-$C_{10}$)cycloalkyl, substituted or unsubstituted ($C_6$-$C_{20}$)aryl, and substituted or unsubstituted ($C_1$-$C_6$)alkyl($C_6$-$C_{20}$)aryl, wherein each substituted $R^3$ has one or more substituents independently selected from F, Cl, Br, and I; and
(D) $R^4$ is selected from H, substituted or unsubstituted ($C_1$-$C_6$)alkyl, substituted or unsubstituted ($C_3$-$C_{10}$)cycloalkyl, substituted or unsubstituted ($C_1$-$C_6$)alkyl($C_3$-$C_{10}$)cycloalkyl, substituted or unsubstituted ($C_6$-$C_{20}$)aryl, substituted or unsubstituted ($C_1$-$C_6$)alkyl($C_6$-$C_{20}$)aryl, substituted or unsubstituted ($C_1$-$C_6$)alkyl($C_2$-$C_6$)alkenyl, and substituted or unsubstituted ($C_1$-$C_6$)alkyl($C_2$-$C_6$)alkynyl, wherein each said $R^4$, which is substituted, has one or more substituents selected from F, Cl, Br, I, CN, $NO_2$, ($C_1$-$C_6$) alkyl, ($C_1$-$C_6$)haloalkyl, ($C_1$-$C_6$)alkyloxy, ($C_1$-$C_6$)haloalkyloxy, ($C_3$-$C_{10}$)cycloalkyl, ($C_3$-$C_{10}$)halocycloalkyl, ($C_6$-$C_{20}$)aryl, and ($C_1$-$C_{20}$)heterocyclyl.

In another embodiment of this invention each $R^1$ is independently selected from H, F, and Cl.

In another embodiment of this invention $R^1$ is H.

In another embodiment of this invention $R^3$ is selected from H, ($C_1$-$C_6$)alkyl, ($C_1$-$C_6$)haloalkyl, and ($C_6$-$C_{20}$)aryl.

In another embodiment of this invention $R^3$ is selected from H, $CF_3$, $CH_2F$, $CHF_2$, $CH_3$, $CH_2CH_3$, $CH(CH_3)_2$, and phenyl.

In another embodiment of this invention $R^3$ is selected from H and $CH_3$.

In another embodiment of this invention $R^4$ is ($C_1$-$C_6$)alkyl ($C_3$-$C_{10}$)cyclohaloalkyl.

In another embodiment of this invention $R^4$ is selected from H, ($C_1$-$C_6$)alkyl, ($C_1$-$C_6$)alkyl($C_6$-$C_{20}$)aryl, ($C_1$-$C_6$)haloalkyl, ($C_1$-$C_6$)alkyl($C_3$-$C_{10}$)cycloalkyl, ($C_3$-$C_{10}$)cycloalkyl-O-($C_1$-$C_6$)alkyl, and ($C_3$-$C_{10}$)cyclohaloalkyl.

In another embodiment of this invention $R^4$ is selected from H, $CH_3$, $CH_2CH_3$, $CH(CH_3)_2$, $CH_2CH(CH_3)_2$, cyclopropyl, ($C_6$-$C_{20}$)aryl, $CH_2$-phenyl, $CH_2$-phenyl-$OCH_3$, $CH_2OCH_2$-phenyl, $CH_2CH_2CH_3$, $CH_2CH_2F$, $CH_2CH_2OCH_3$, $CH_2$cyclopropyl, and cyclopropyl-O-$CH_2CH_3$.

In another embodiment of this invention $R^4$ is selected from H, $CH_3$, $CH_2CH_3$, $CH(CH_3)_2$, $CH_2CH(CH_3)_2$, $CH_2CH_2CH_3$, cyclopropyl, $CH_2$cyclopropyl, and $CH_2CH=CH_2$, $CH_2C\equiv CH$.

In another embodiment of this invention molecules having a structure according to compound (III) are disclosed as intermediates useful for the synthesis of pesticidal thiazole amides.

In general, S—$R^2$ is a leaving group wherein $R^2$ is part of the leaving group that does not substantially and adversely affect the desired reaction. It is desirable that $R^2$ is a group that beneficially affects the volatility of the thio by-product of the reaction.

In step a1, compounds (I) and (IIa) are reacted to produce compound (IIb). The reaction can be conducted at ambient temperature and under ambient pressure, but higher or lower temperatures and pressures can be used, if desired. Compounds (IIa) and (IIb) can be in the form of a salt or free base. The reaction is conducted in the presence of a base such as triethylamine, when compound (IIa) is a salt. The reaction is conducted in a polar protic solvent. Examples of such solvents include, but are not limited to, formic acid, n-butanol, isopropanol, n-propanol, ethanol, methanol, acetic acid, and water. Currently, methanol is preferred.

In step a2, compounds (IIb) and (IIc) are reacted to produce compound (III). The reaction can be conducted at ambient temperature and under ambient pressure, but higher or lower temperatures and pressures can be used, if desired, such as temperatures from about 50° C. to about 70° C. The reaction is conducted in a polar solvent such as an ether or an alcohol. Examples of such solvents include, but are not limited to, dichloromethane, tetrahydrofuran, ethyl acetate, acetone, dimethylformamide, acetonitrile, and dimethyl sulfoxide, n-butanol, isopropanol, n-propanol, ethanol, and methanol. Currently, methanol is preferred. It is also useful to use a excess molar amount of compound (IIc) to (IIb), such as about 25:1 (IIc):(IIb), however, molar ratios from about 3:1 to about 20:1 can be used, and preferably molar ratios from 10:1 to 15:1 are used.

In step b, compound (III) is cyclized using a dehydrating agent. Examples of such dehydrating agents include, but are not limited to, $POCl_3$, $H_2SO_4$, $SOCl_2$, $P_2O_5$, polyphosphoric acid, p-toluene sulfonic acid, and trifluoroacetic anhydride. The reaction can be conducted at ambient temperature and under ambient pressure, but higher or lower temperatures and pressures can be used, if desired. Currently, it is preferred if a temperature higher than ambient temperature is used, preferably, up to and including the boiling point of the solution, for example, a temperature from about 60° C. to about 120° C. can be used. The reaction is conducted in a polar aprotic solvent. Currently, acetonitrile is preferred.

An advantage with these processes is that in compound (IV)—if $R^3$ is H, it can be halogenated. Consequently, at this point $R^3$ additionally now includes F, Cl, Br, and I (see Scheme Two).

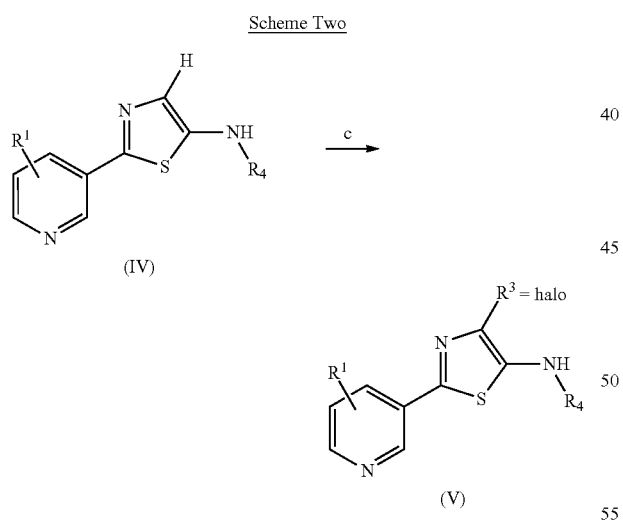

In step c, any halogenating agent can be used, for example, 1-chloropyrrolidine-2,5-dione, N-bromosuccinimide, and 1-chloromethyl-4-fluoro-1,4-diazoniabicyclo[2.2.2]octane bis(tetrafluoroborate). Polar solvents can be used such as dichloromethane, tetrahydrofuran, ethyl acetate, acetone, dimethylformamide, acetonitrile, and dimethyl sulfoxide. Currently, dichloromethane is preferred. The reaction can be conducted are ambient temperature and pressure, but higher or lower temperatures and pressures can be used, if desired. Currently, temperatures from about 0° C. to about ambient are preferred.

In another embodiment of this invention $R^3$ is preferably Cl.

Compound (IV) or compound (V) can be further reacted to form certain pesticides disclosed in WO 2010/129497 (the entire disclosure of which is incorporated herein by reference).

EXAMPLES

The examples are for illustration purposes and are not to be construed as limiting the invention disclosed in this document to only the embodiments disclosed in these examples.

Starting materials, reagents and solvents which were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Molecules are given their known names, named according to naming programs within ISIS Draw, ChemDraw or ACD Name Pro. If such programs are unable to name a molecule, the molecule is named using conventional naming rules. All NMR are in ppm (δ) and were recorded at 300, 400, or 600 MHz unless otherwise stated.

Example 1

Preparation of N-ethyl-2-(pyridin-3-carbothioamido)acetamide

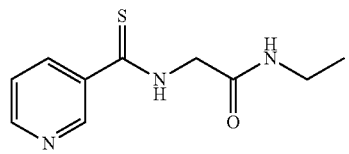

Step 1: Preparation of methyl 2-pyridine-3-carbothioamidoacetate:

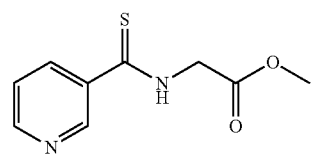

To a dry 50 ml round bottom flask equipped with magnetic stirrer, nitrogen inlet, bleach scrubber, thermometer, and addition funnel, was charged methyl pyridine-3-carbodithioate (2.0 g, 11.82 mmol), methyl 2-aminoacetate hydrochloride (1.48 g; 11.82 mmol) and 20 ml of methanol. Triethylamine (1.20 g, 11.82 mmol) in methanol (5 mls) was added, dropwise. The mixture was stirred at ambient temperature for 16 hours. The reaction mixture was poured into 200 ml of water, and the aqueous mixture was extracted with 3×50 ml of ethyl acetate. The combined organic extracts were washed with water and brine, dried over anhydrous $MgSO_4$, filtered, and concentrated under reduced pressure on a rotary evaporator. The crude product was then dissolved in dichloromethane and chromatographed on silica gel (80 g ISCO cartridge) with a gradient of 100% hexanes to 100% ethyl acetate over 20 minutes. The pure fractions were combined and then solvent evaporated under vacuum to afford the title compound as a thick yellow oil (1.6 g, 64%): $^1$H NMR (400 MHz, CDCl$_3$) δ 8.96 (dd, J=2.4, 0.8 Hz, 1H), 8.68 (dd, J=4.8, 1.7 Hz, 1H), 8.47 (bs, 1H), 8.16 (ddd, J=8.0, 2.4, 1.7 Hz, 1H), 7.35 (ddd, J=8.0, 4.8, 0.9 Hz, 1H), 4.59 (d, J=4.7 Hz, 2H), 3.86 (s, 3H); ESIMS m/z 209.17 ([M-H]$^-$).

Step 2: Preparation of N-ethyl-2-(pyridin-3-carbothioamido) acetamide:

To a cooled (−40° C.) solution of methyl 2-(pyridine-3-carbothioamido)acetate (2.5 g, 11.89 mmol) in 20 ml of methanol in a 45 ml Parr reactor was added ethylamine (6.6 g, 146.00 mmol). The Parr reactor was sealed and heated to 60° C. for 5 hours. To this solution was added 5 g of silica gel, and the mixture evaporated to dryness. The sample was chromatographed on the ISCO using a gradient of ethyl acetate and dichloromethane, followed by 100% ethyl acetate. The solvent was removed in vacuo to afford the title compound as a yellow solid (1.8 g; 68%); mp 136-138° C.; $^1$H NMR (400 MHz, d$_6$-DMSO) δ 10.62 (s, 1H), 8.94 (dd, J=2.4, 0.7 Hz, 1H), 8.68 (ddd, J=13.4, 4.8, 1.7 Hz, 1H), 8.15-7.94 (m, 2H), 7.49 (tdd, J=8.0, 4.8, 0.8 Hz, 1H), 4.34 (s, 2H), 3.21-3.03 (m, 2H), 1.03 (t, J=7.2 Hz, 3H); $^{13}$C NMR (101 MHz, DMSO-d$_6$) δ 195.74 (s), 166.34 (s), 151.87 (s), 151.29 (s), 148.66 (s), 147.70 (s), 136.20 (s), 135.02 (d, J=18.7 Hz), 123.37 (s), 123.00 (s), 48.79 (s), 40.13 (s), 39.93 (s), 39.72 (s), 39.51 (s), 39.30 (s), 39.09 (s), 38.88 (s), 33.51 (s), 14.71 (s).

Example 2

Preparation of N-(4-chloro-2-(pyridin-3-yl)thiazol-5-yl)-N,2-dimethyl-3-(methylthio)propanamide

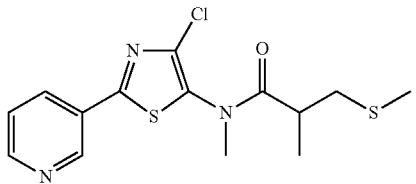 [SMILES: CSCC(C)C(=O)N(C)c1sc(-c2cccnc2)nc1Cl]

Step 1: Preparation of N-methyl-2-(pyridin-3-yl)thiazol-5-amine:

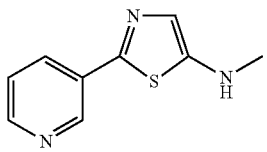

To a dry 2 L round bottom flask equipped with mechanical stirrer, addition funnel and reflux condenser was charged N-methyl-2-(pyridine-3-carbothioamido)acetamide (100 g, 478 mmol) and acetonitrile (1 L). To this mixture was added phosphorus oxychloride (256 g, 1672 mmol) portionwise over 10 minutes. The reaction mixture was stirred at ambient temperature for 10 minutes during which time a slight exotherm occurred from 22° C. to 34° C. The reaction mixture was heated to 85° C. (refluxing gently). After 3 hours, all of the solid had dissolved, forming a dark amber solution. Analysis of an aliquot by TLC (70% ethyl acetate : 30% hexanes) after 4 hours indicated that the reaction was essentially complete. The reaction mixture was allowed to cool to 25° C. and the solvent removed by rotary evaporation. The residue was dissolved in water and treated with solid sodium bicarbonate until slightly basic (pH~8) with continuous stirring. A brown precipitate started to form after a few minutes. The mixture was continued to stir at 25° C. for 16 hours. The brown solid was collected by vacuum filtration and washed with water. This gave a tan solid wet cake (91 g) which was then dried in vacuo at 40° C. to a constant weight. This gave N-methyl-2-(pyridin-3-yl)thiazol-5-amine as a sand colored solid (68.5 g, 75% yield); mp 140-141° C.; $^1$H NMR (400 MHz, CDCl$_3$) δ 8.98 (dd, J=2.3, 0.7 Hz, 1H), 8.53 (dd, J=4.8, 1.6 Hz, 1H), 8.07 (ddd, J=8.0, 2.2, 1.7 Hz, 1H), 7.40-7.21 (m, 1H), 6.96 (s, 1H), 4.18 (s, 1H), 2.96 (s, 3H); $^{13}$C NMR (101 MHz, CDCl$_3$) δ153.23, 149.15, 146.54, 132.23, 130.47, 123.65, 121.20, 34.48; Anal. Calc'd. for C$_9$H$_9$N$_3$S: C, 56.52; H, 4.74; N, 21.97; S, 16.77. Found: C, 56.31: H, 4.74; N, 21.81; S, 16.96.

Step 2: Preparation of 4-chloro-N-methyl-2-(pyridin-3-yl) phiazol-5-amine:

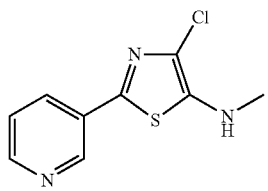

To a dry 100 ml round bottom flask equipped with magnetic stirrer, thermometer, and nitrogen inlet was charged N-methyl-2-(pyridin-3-yl)thiazol-5-amine (0.528 g, 2.76 mmol) and dichloromethane (50 mls). The resulting solution was cooled to 5° C., followed by the portionwise addition of solid N-chlorosuccinimide (0.312 g, 2.76 mmol). After all of the chlorinating agent was added, a dark brown solution formed. The solution was stirred at 5° C. for 20 minutes, then analyzed an aliquot by HPLC (YMC AQ column 5% ACN 95% water-0.05% TFA to 95%ACN 5% water with 0.05% TFA over 20 Min @ 1.0 ml/min) HPLC analysis showed no starting material and one major product. The reaction mixture was poured into a separatory funnel containing dichloromethane (50 mls) and washed with water (2×10 mls) followed by saturated aqueous sodium chloride solution (10 mls). The organic phase was dried over anhydrous magnesium sulfate, filtered, and rotary evaporated to give a powdery brown solid (0.51 g). The solid was purified on a ISCO Combiflash Rf (silica gel 80 g cartridge, mobile phase A=hexane, B=ethyl acetate, gradient 0% B to 100% B over 20 minutes). The tubes containing the desired material were combined and rotary evaporated to afford 4-chloro-N-methyl-2-(pyridin-3-yl)thiazol-5-amine as a canary yellow solid (0.32 g, 51% yield); $^1$H NMR (400 MHz, CDCl$_3$) δ8.97 (dd, J=2.3, 0.7 Hz, 1H), 8.54 (dd, J=4.8, 1.6 Hz, 1H), 8.07 (ddd, J=8.0, 2.3, 1.6 Hz, 1H), 7.45-7.14 (m, 1H), 4.07 (dd, J=40.5, 38.0 Hz, 1H), 3.03 (d, J=5.3 Hz, 3H); $^{13}$C NMR (101 MHz, CDCl$_3$) δ149.55, 146.03, 145.60, 145.28, 131.73, 129.71, 123.64, 117.37, 35.75; Anal. Calc'd. for C$_9$H$_8$ClN$_3$S: C, 49.89; H, 3.57; N, 18.62; S, 14.21. Found: C, 48.03: H, 3.64; N, 18.42; S, 14.23.

Step 3: Preparation of N-(4-chloro-2-(pyridin-3-yl)thiazol-5-yl)-N,2-dimethyl-3-(methylthio)propanamide:

To a dry 500 ml round bottom flask equipped with magnetic stirrer, thermometer, and nitrogen inlet was added 4-chloro-N-methyl-2-(pyridin-3-yl)thiazol-5-amine (22 g, 97 mmol) and dichloromethane (250 mls). The suspension was stirred at ambient temperature while pyridine (8.48 g, 107 mmol) and DMAP (1.20 g, 9.75 mmol) were added. To this suspension was added 2-methyl-3-(methylthio)propanoyl chloride (17.8 g, 117 mmol) over 5 minutes. During the addition all solids went into solution and the reaction was exothermic from 20° C. to 30° C. The reaction was stirred at ambient temperature for 16 h. The mixture was checked by HPLC (YMC AQ column 5% ACN 95% water-0.05% TFA to 95%ACN 5% water with 0.05% TFA over 20 Min @ 1.0 ml/min) which showed complete conversion of all starting material. The reaction mixture was diluted with dichloromethane and water was then added. The mixture was poured into a separatory funnel with dichloromethane and water and the layers separated. The organic phase was washed with brine, dried over anhydrous magnesium sulfate, filtered, and rotary evaporated to afford 33.6 g of a dark oil. The oil was purified on an ISCO Combiflash Rf (330 g silica gel cartridge, mobile phase A=hexane, B=ethyl acetate, gradient 0% B to 100% B over 20 minutes). The fractions were collected into 25 mls test tubes. The tubes containing the desired product were combined and the solvent removed by rotary evaporation. This afforded 22.8 g of a thick yellow liquid in 68.4% isolated yield. The entire sample crystallized and hexane (200 mls) was added to give a slurry. The slurry was vacuum filtered and the solid allowed to air dry. This gave N-(4-chloro-2-(pyridin-3-yl)thiazol-5-yl)-N,2-dimethyl-3-(methylthio)propanamide as an off-white solid; mp 75-80° C.; $^1$H NMR (400 MHz, CDCl$_3$) δ 9.12 (d, J=1.4 Hz, 1H), 8.73 (d, J=3.8 Hz, 1H), 8.34-8.09 (m, 1H), 7.43 (dd, J=7.9, 4.9 Hz, 1H), 3.30 (s, 3H), 3.06-2.70 (m, 2H), 2.49 (d, J=7.4 Hz, 1H), 2.04 (s, 3H), 1.21 (d, J=6.4 Hz, 3H); $^{13}$C NMR (101 MHz, DMSO-d$_6$) δ175.22, 162.37, 151.91, 146.53, 136.46, 134.64, 133.35, 127.98, 124.27, 37.47, 36.71, 36.47, 17.56, 15.44; Anal. Calcd. for $C_{14}H_{16}ClN_3OS_2$: C, 49.18; H, 4.72; N, 12.29; S, 18.76. Found: C, 49.04: H, 4.68; N, 12.29; S, 18.68.

What is claimed is:

1. A process comprising

Scheme One

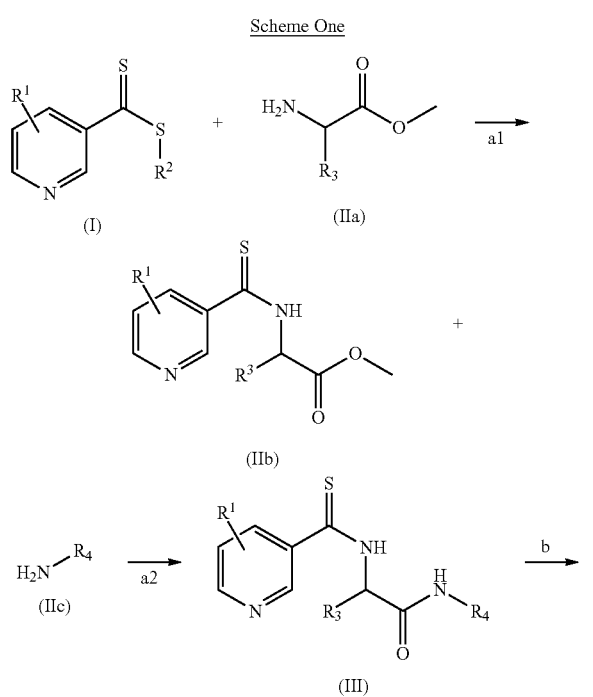

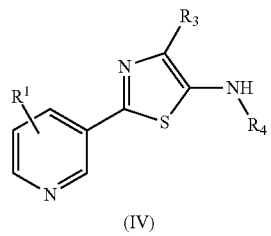

(i) reacting compound (I) with compound (IIa) to produce compound (IIb) wherein said reacting is conducted at ambient temperature and pressure and in a polar protic solvent; followed by (ii) reacting compound (IIb) with compound (IIc) to product compound (III) wherein said reacting is conducted at ambient temperature and pressure and in a polar solvent; followed by (iii) cyclizing compound (III) using a dehydrating agent to produce compound (IV) wherein said reacting is conducted at ambient temperature and pressure and in a polar aprotic solvent;

wherein (A) each $R^1$ is H;
(B) $R^2$ is a $(C_1$-$C_6)$alkyl;
(C) $R^3$ is H; and
(D) $R^4$ is a $(C_1$-$C_6)$alkyl.

2. A process according to claim 1, wherein step a1 said polar protic solvent is formic acid, n-butanol, isopropanol, n-propanol, ethanol, methanol, acetic acid, water, or a mixture thereof.

3. A process according to claim 1, wherein step a1 said polar protic solvent is methanol.

4. A process according to claim 1 wherein step b compound (III) is cyclized using a dehydrating agent selected from POCl$_3$, H$_2$SO$_4$, SOCl$_2$, P$_2$O$_5$, polyphosphoric acid, p-toluene sulfonic acid, trifluoroacetic anhydride, or a mixture thereof.

5. A process according to claim 1, wherein step b is conducted at a temperature from about 60° C. to about 120° C.

6. A process according to claim 1, wherein step b said polar aprotic solvent is acetonitrile.

7. A process according to claim 1, said process further comprising halogenating said $R^3$ to F, Cl, Br, or I.

8. A process according to claim 7, wherein said halogenating is conducted in a solvent selected from dichloromethane, tetrahydrofuran, ethyl acetate, acetone, dimethylformamide, acetonitrile, and dimethyl sulfoxide.

9. A process according to claim 8, wherein said solvent is dichloromethane.

10. A process according to any one of claims 7, 8, and 9, wherein said halogenating is conducted at a temperature from 0° C. to ambient.

11. A process according to any one of claims 7, 8, and 9, wherein $R^3$ is Cl.

* * * * *